United States Patent
Buczkowski et al.

(10) Patent No.: US 8,330,946 B2
(45) Date of Patent: Dec. 11, 2012

(54) SILICON FILTER FOR PHOTOLUMINESCENCE METROLOGY

(75) Inventors: Andrzej Buczkowski, Bend, OR (US); Christopher Raymond, Bend, OR (US)

(73) Assignee: Nanometrics Incorporated, Milpitas, CA (US)

( * ) Notice: Subject to any disclaimer, the term of this patent is extended or adjusted under 35 U.S.C. 154(b) by 393 days.

(21) Appl. No.: 12/638,748

(22) Filed: Dec. 15, 2009

(65) Prior Publication Data

US 2011/0141460 A1    Jun. 16, 2011

(51) Int. Cl.
*G01N 21/00* (2006.01)
(52) U.S. Cl. .................................................. 356/237.1
(58) Field of Classification Search .................. None
See application file for complete search history.

(56) References Cited

U.S. PATENT DOCUMENTS

| 6,911,347 | B2 * | 6/2005 | Higgs ............................... 438/7 |
| 7,113,276 | B1 | 9/2006 | Higgs et al. |
| 7,504,642 | B2 | 3/2009 | Hummel et al. |
| 2007/0000434 | A1 | 1/2007 | Buczkowski |
| 2008/0213926 | A1 * | 9/2008 | Tajima et al. ................... 438/16 |

FOREIGN PATENT DOCUMENTS

WO    WO 98/11425    3/1998

* cited by examiner

*Primary Examiner* — Tu Nguyen
(74) *Attorney, Agent, or Firm* — Silicon Valley Patent Group LLP

(57) ABSTRACT

A method and apparatus identifies defects in a sample using photoluminescence with a silicon filter to filter out the primary excitation light from the return light received by the detector. The silicon filter passes the light emitted by the sample in response to the excitation light, while absorbing the lower wavelength excitation light that is reflected by or transmitted through the sample. The silicon filter has introduced impurities that reduce the recombination lifetime which reduces or eliminate photoluminescence in the silicon filter in response to the excitation light, thereby improving the signal to noise ratio of the signal received by the detector.

30 Claims, 2 Drawing Sheets

SILICON FILTER FOR PHOTOLUMINESCENCE METROLOGY

BACKGROUND

Photoluminescence imaging and spectroscopy is a contactless, nondestructive method of probing the electronic structure of materials, such as silicon semiconductor wafers, solar cells, as well as other workpieces and materials. In a typical photoluminescence process, light is directed onto a wafer or other workpiece (hereinafter collectively referred to as a "sample"), where at least some of the light is absorbed. The absorbed light imparts excess energy into the material via a process of "photo-excitation." This excess energy is dissipated by the sample through a series of pathways; one such pathway is the emission of light, or photoluminescence. The intensity and spectral content of this photoluminescence is directly related to various material properties of the sample.

Photoluminescence imaging processes may be used to identify and quantify defects and contaminants present in the sample based on spatial variations in the photoluminescence images produced. One photoluminescence imaging process, as described in International Application Number PCT/GB97/02388 (publication number WO 98/11425), which is incorporated herein by reference, involves probing the surface and/or the sub-surface bulk region of the sample with one or more lasers of varying excitation wavelengths. A laser of a given wavelength is directed into the sample and penetrates the sample to a given depth. Return light emitted from excited regions of the sample is detected and quantified by a detection system. Images of the measured return light, including spatial images of defects and contaminants in the sample, may then be produced by the detection system or by an associated image-producing system.

Samples, such as solar materials or cells when tested using photoluminescence imaging, may reflect a significant portion of light used for sample excitation, e.g., approximately 1%-35% of the excitation light is reflected. At the same time, photoluminescence radiation generated in the sample may be significantly lower in intensity than the excitation light, e.g., by multiple orders of magnitude (>10). As a result, photoluminescence radiation is heavily energy "contaminated" by the reflected excitation light. Conventional filters do not have enough attenuation to adequately eliminate the excitation light. Thus, there is a need to filter the primary excitation light from the photoluminescence signal.

SUMMARY

A method and apparatus identifies defects in a sample using photoluminescence with a silicon filter to filter out the primary excitation light from the return light received by the detector. The silicon filter passes the light emitted by the sample in response to the excitation light, while absorbing the lower wavelength excitation light that is reflected by or transmitted through the sample. The silicon filter may be contaminated, e.g., with a heavy metal such as gold or platinum, to reduce the recombination lifetime to reduce or eliminate photoluminescence in the silicon filter in response to the excitation light, thereby improving the signal to noise ratio of the signal received by the detector. The silicon filter may be further optimized by coating one or both sides of the silicon filter with an antireflection coating, or by texturing or patterning the filter to enhance the desired optical performance.

DETAILED DESCRIPTION

Figure 1:
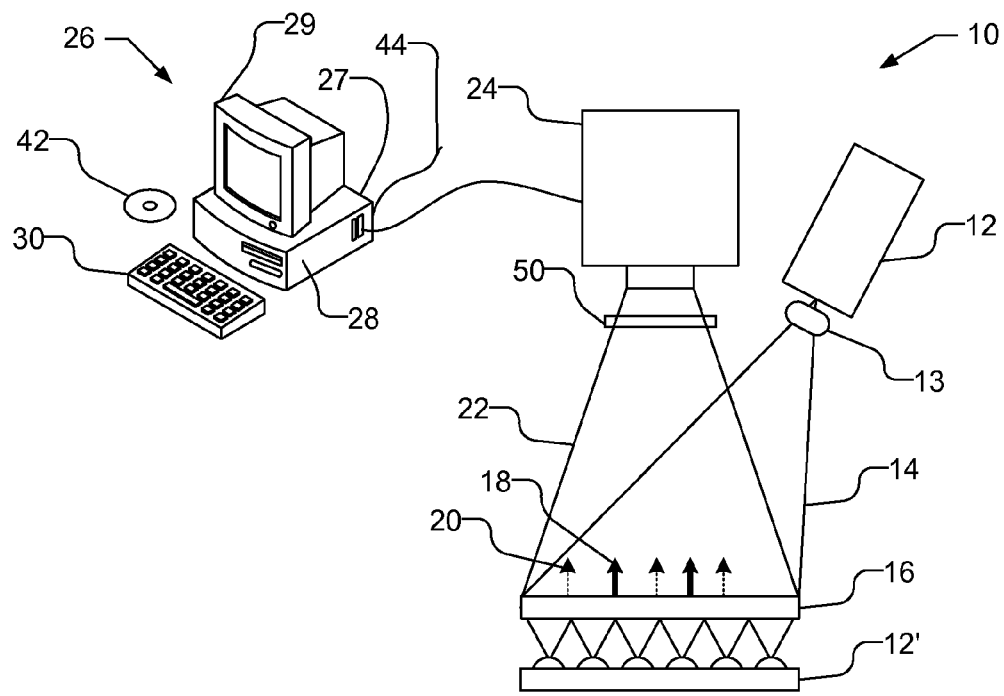
FIG. 1 schematically illustrates the basic components of a photoluminescence imaging system that uses a silicon filter to filter out the excitation light that is reflected by or transmitted through the sample.

FIG. 1 schematically illustrates the basic components of a photoluminescence system 10 for imaging or spectroscopy. The photoluminescence system 10 includes a light source 12, such as a laser, laser diode or other suitable light source, such as an LED array. The light source 12 may produce excitation light in the infrared spectrum, e.g., 808 nm, but other wavelengths may be used as well, e.g., 400 nm-960 nm. The photoluminescence system 10 may operate either in reflectance mode using light source 12 or in transmission mode using light source 12', which is illustrated as an LED array. Other types of light sources, such as a laser, laser diode may be used with photoluminescence system 10 in either reflection or transmission mode. The light source 12 generates excitation light 14 that illuminates the sample either directly or via one or more intervening optical components, such as illumination optic 13. Illumination optic 13 may be, e.g., a collimator or diverging lens or other optical component, that may be used to illuminated the full surface area of the sample 16 simultaneously. The term "sample," as used herein, includes any sample upon which photoluminescence imaging may be performed including a silicon semiconductor sample, solar cell panel, or other microelectronic, micro electromechanical, or optoelectronic substrate or other sample.

The incident excitation light 14 penetrates the sample 16, where at least a portion of the incident excitation light 14 is absorbed by the sample 16 and is emitted from the sample 16 as photoluminescent return light 18 at higher wavelengths than the excitation light 14. For example, the photoluminescent radiation emitted by sample 16 may be a spectrum centered around 1100 nm. The emitted photoluminescent return light 18 includes data identifying defects located in the sample 16. The term "defects," as used herein, includes any contaminants, flaws, discontinuities, impurities, and/or other imperfections present in a sample 16. Additionally, a portion of the excitation light 14 is reflected by the sample 16 or transmitted by the sample 16 if light source 12' is used, as illustrated by dotted arrows 20. The photoluminescent return light 18 and the reflected or transmitted excitation light 20 together form combined return light 22.

The combined return light 22 enters a filter 50 connected to and/or optically aligned with a detector 24, such as a CCD array or other detection system suitable for imaging infrared radiation. By way of example, the detector 24 may be a low readout noise, low dark current, silicon or InGaAs sensor based camera with high resolution. If desired, the detector 24 may include thermo-electrical sensor cooling, with or without an additional photon or electron gain module. A computer 26 is preferably included in, or is connected to or otherwise associated with, the detector 24 for processing data detected by the detector 24. The computer 26, which includes a processor 27 with memory 28, as well as a user interface including e.g., a display 29 and input devices 30. A computer-usable medium 42 having computer-readable program code embodied may be used by the computer 26 for causing the processor to control the device 10 and to perform the functions including the analysis described herein. The data structures and software code for automatically implementing one or more acts described in this detailed description can be implemented by one of ordinary skill in the art in light of the present disclosure and stored, e.g., on a computer readable storage medium 42, which may be any device or medium that can store code and/or data for use by a computer system such as processor 28. The computer-usable medium 42 may be, but is not limited to, magnetic and optical storage devices such as disk drives, magnetic tape, compact discs, and DVDs (digital versatile discs or digital video discs). A communication port 44 may also be used to receive instructions that are used to program the computer 26 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Figure 2A:
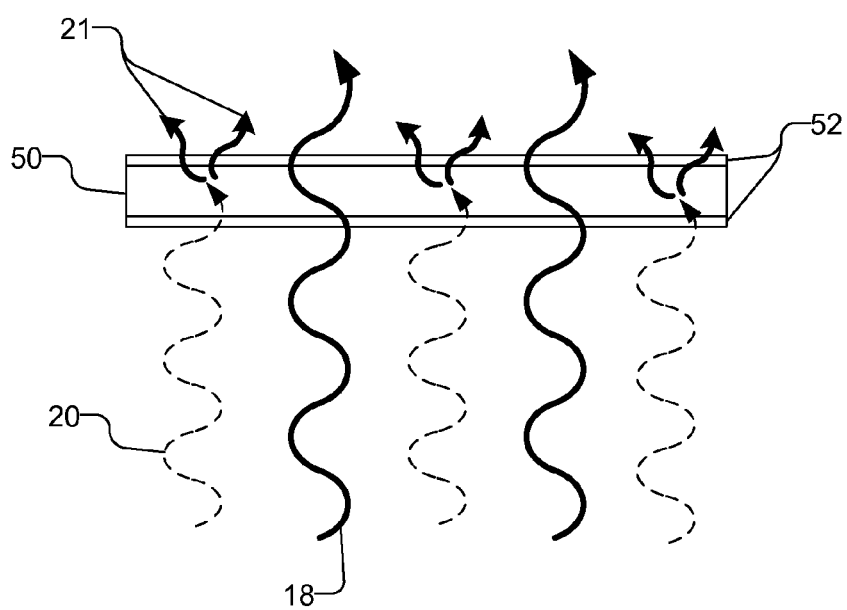
FIG. 2A illustrates a side view of the silicon filter with combined return light including the return light from the sample as well as the reflected or transmitted excitation light that causes photoluminescence in the silicon filter.
Figure 2B:
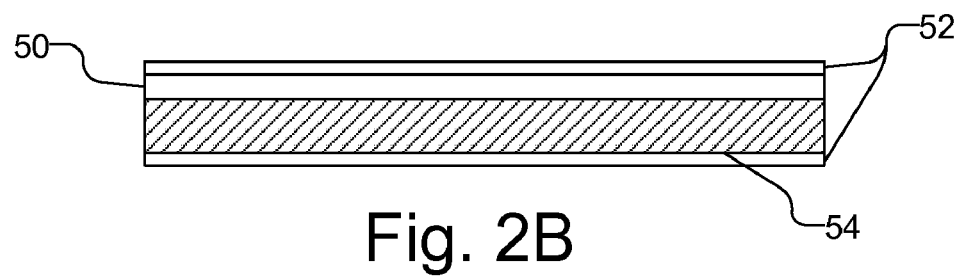
FIG. 2B illustrates a cross-sectional view of a silicon filter similar to that shown in FIG. 2A, but with a transparent isolative substrate.

The filter 50 is a high pass filter that blocks the excitation light 20 while passing the higher wavelength photoluminescent return light 18 emitted by the sample 16. FIG. 2A illustrates a side view of the filter 50 with excitation light 20 and photoluminescent return light 18. The filter 50 is a formed from semiconductor materials with an indirect bandgap. For example, one type of semiconductor material with an indirect bandgap that may be used is silicon, but other materials may be used if desired. For the sake of reference, filter will be referred to herein as silicon filter 50. As illustrated in cross-sectional view FIG. 2B, in some embodiments, the filter 50 include additional materials such as a transparent isolative substrate 54, such as sapphire, which may be particularly desirable if the thickness of the filter 50 is thin and requires mechanical support. By way of example, the silicon filter 50 may be a single crystal silicon wafer that is sized to match the lens design or filter holder for the detector 24. For example, a silicon wafer filter may be 2 inches in diameter. Semiconductor materials with an indirect bandgap, such as silicon, strongly absorb photons at energies higher than the semiconductor bandgap, but are relatively transparent for photons with energies lower than the bandgap.

As illustrated in FIG. 2A, the band-edge for the silicon filter 50 permits the absorption of the excitation light 20, which has a wavelength of, e.g., 808 nm, while transmitting the photoluminescent return light 18, which has wavelengths centered around approximately 1100 nm. It should be noted that conventional silicon windows that are used as filters are typically used in applications where near-infrared filtering in the 2000 nm to 5000 nm range transmission is of interest. The silicon filter 50 is tuned for passing wavelengths less than 2000 nm, and more specifically, wavelengths less than 1500 nm and particularly wavelengths around 1100 nm. Tuning may be achieved through appropriate selection of filter thickness so that the filter is thick enough to absorb the excitation light reflected from the sample to a desired degree, e.g., at least 10 orders of magnitude, while at the same time being thin enough to transmit the photoluminescent return light 18 from the sample 16. Because a thicker filters absorbs more of the reflected (undesirable) excitation light 20, but also absorbs more of the desired photoluminescent return light 18; a trade-off in filter thickness is made. Additional tuning may be achieved by reducing the photoluminescent return light 18 reflection from the filter by coating the silicon filter 50 with an antireflection layer designed for maximum transparency at the wavelength of interest (1100 nm). The antireflection coating can be multilayer, such as it also reflects the undesired excitation light.

The thickness of the silicon filter 50 is dependent on the wavelength(s) of the excitation light and the return light from the sample 16. The filter thickness maybe optimized for achieving the best characteristics of transmission of the wavelengths of the desired photoluminescent return light 18 from the sample 16 and attenuation of the wavelengths of the excitation light 20. For example, if the light source 12 produces excitation light 14 in UV wavelengths, a thin silicon filter, e.g., 10 μm would be adequate. However, with longer wavelength excitation light, a silicon filter of greater thickness is used. For example, for an excitation light 14 of 808 nm, a 0.2 mm silicon filter may be used. The transmission-attenuation characteristics for the silicon filter 50 maybe a function of the state of the sample to be measured (for example raw substrate or substrate after AR coating), the wavelength used for sample excitation, and/or detector 24 (detector) design. For example, raw silicon samples may reflect about 30%, while AR coated materials may reflect less than 5% of the excitation radiation. Therefore, a silicon filter 50 designed for characterization of raw materials will be thicker than a silicon filter 50 used for analyzing materials coated with antireflective coatings. Similarly, shorter excitation wavelengths are absorbed more strongly than longer wavelengths, therefore, when, for example, 760 nm excitation is used instead of 808 nm, the silicon filter 50 may be thinner.

Both sides of the silicon wafer should be flat and highly polished to reduce or eliminate scatter. An anti-reflective (AR) coating 52, e.g., of SiN or $SiO_2$, may be applied to one or both sides of the silicon filter 50, to reduce the reflection of the photoluminescence signal from the sample 16. Additionally, the AR coating 52 on the filter 50 front side, e.g., the side facing the sample 16, should be optimized to increase the reflection of excitation light 20 to reduce penetration of this radiation into the filter. The AR coating optimization is done by depositing a single or multiple layer of materials with appropriate n, k (optical constants) to match the n, k of the substrate, silicon in our case. A single AR coating layer can be used to maximize the transmission at a given wavelength (e.g., 1100 nm), while a multilayer AR coating may be used for additional reflection of the excitation light (e.g., rejection of for example 808 nm).

Figure 2C:
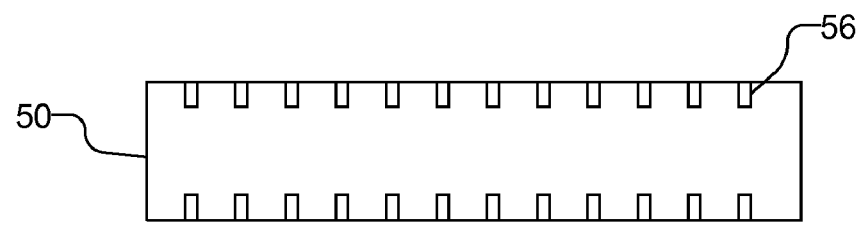
FIG. 2C illustrates a cross-sectional view of a silicon filter with texturing or patterning, e.g., in the form of a photonic crystal structure.

Further improvements to the performance of the silicon filter 50 may be realized by texturing or patterning one or both surfaces of the silicon filter 50 as illustrated in cross-sectional view in FIG. 2C. One method of patterning may involve the use of a photonic crystal structure. A photonic crystal is a periodic array of optical structures 56, like holes or posts, whose geometry is designed to affect the motion of photons in a particular manner. Through proper design, photonic crystals may be used as high-reflecting mirrors or optical filters for attenuating or transmitting particular wavelengths of light. For the present invention, a photonic crystal can be used to highly reflect the excitation light 20, while transmitting photoluminescent photons in the photoluminescent return light 18. Because photonic crystals can be made with inexpensive technologies like imprint lithography, they may offer technical and cost advantages when compared to other filtering technologies.

The silicon filter 50, however, photoluminesces and, thus, will absorb photons of the excitation light 20 and in response will emit higher wavelength photoluminescent light, as illustrated by arrows 21 in FIG. 2A. The photoluminescent light from the silicon filter 50 will be convolved with the photoluminescent return light 18 from the sample thereby introducing measurement artifacts. Accordingly, it is desirable to reduce the photoluminescent level of the silicon filter 50 to a negligible level, e.g., below 10% of the level observed in bare samples 16, e.g., bare solar cell materials, or below 1% for passivated samples 16, e.g., ARC coated materials. The photoluminescent level of the silicon filter 50 may be reduced by reducing the recombination lifetime in the silicon filter 50 by introducing impurities into the silicon filter 50.

Figure 3:
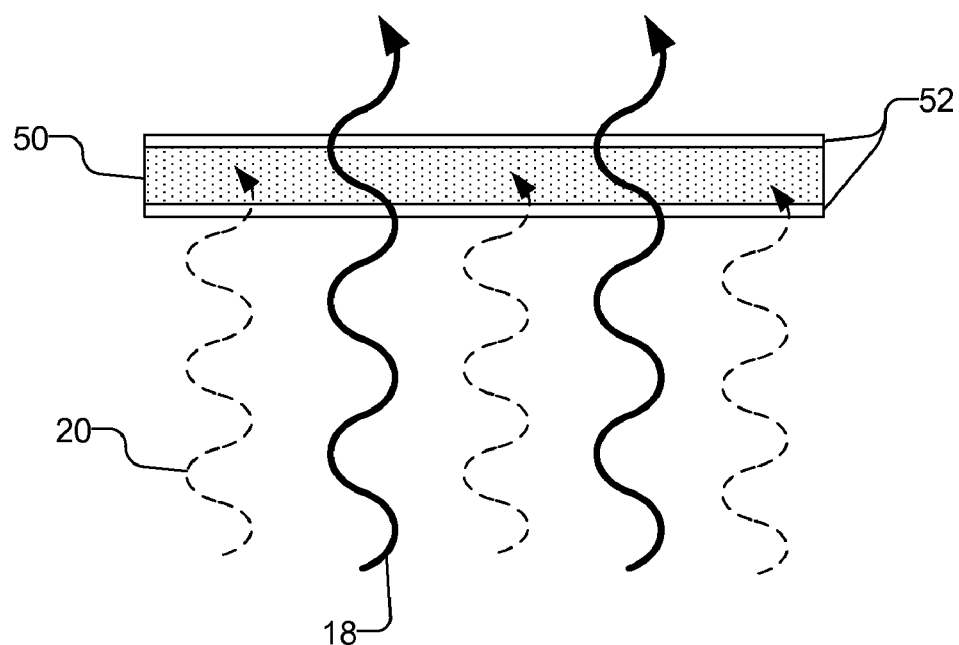
FIG. 3 illustrates a side view of the silicon filter contaminated with a heavy metal to reduce the recombination lifetime to reduce or eliminate photoluminescence in the silicon filter caused by reflected or transmitted excitation light in the combined return light.

FIG. 3 illustrates a side view of a silicon filter 50 with introduced impurities that reduce the recombination lifetime along with the attenuated excitation light 20 and the transmitted photoluminescent return light 18. The introduction of impurities that reduce the recombination lifetime in the silicon filter 50 may be accomplished in several different manners. For example, impurities may be introduced by ion implantation of the silicon filter with foreign materials. For example, the silicon filter may be implanted with one or more heavy metals, such as gold or platinum. If desired, other materials besides heavy metals may alternatively be used. The use of heavy metals to introduce impurities into the silicon filter 50 is particularly appropriate with a relatively thick filter, e.g., at least 200 µm thick, because the heavy metal will lower the lifetime throughout the filter volume. The contamination with heavy metals may be performed by implanting the heavy metals, e.g., with a dose in a range of 5E9 cm$^2$ to 5e13 cm$^2$. The implantation energy may exceed 50 keV to help with achieving high beam currents. The entire area of the silicon filter 50 that will be exposed to the combined return light 22 is implanted. The contamination is driven-in by post implantation at T>1100° C. for times of 1 hour or more or at a temperature and time adequate to diffuse the contaminants through the filter 50.

Alternatively, the contamination with one or more heavy metals may also be performed by evaporating or sputtering or otherwise depositing the contaminating material, e.g., 100 nm of Gold or 10 nm of Platinum on the surface of the silicon filter 50. The contamination is driven-in by post deposition annealing at T>1100° C. for times of 1 hour or more or at a temperature and time adequate to diffuse the contaminants through the filter 50.

In another embodiment, the introduction of impurities to the silicon filter 50 may be performed through thermal engineering. For example, the silicon may be doped with oxygen, carbon and/or nitrogen during crystal growth. The dopants may agglomerate or precipitate through thermal annealing to produce bulk micro defects, which reduce the recombination lifetime.

In yet another embodiment, impurities are introduced to the silicon filter by ion implantation of foreign atoms to damage the silicon crystal. In one embodiment, the foreign atom introduced into the silicon filter through ion implantation may be silicon atoms. The silicon filter, however is not annealed in this case, relying on the disrupted crystal lattice as the mechanism to reduce the recombination lifetime.

Both surfaces of the silicon filter 50 are then re-polished after the diffusion of the contamination to achieve a mirror-like surface quality. The anti-reflective coating 52 may be applied after re-polishing.

As illustrated in FIG. 3, with the recombination lifetime reduced by introducing a contamination such as a heavy metal into the silicon, the photoluminescence in the silicon filter 50 is reduced or eliminated thereby improving the signal to noise ratio of the signal received by the detector 24.

The detector 24 receives the filtered return light and provides data to the computer 26. Thus, only defect data or intensity values characteristic of the sample 16 is detected and processed, without the excitation light and with little or no photoluminescent light produced by the silicon filter 50. The computer 26 processes the received defect data to produce a defect data characteristic of the sample. Processing photoluminescence defect data is described in U.S. Pat. No. 7,504,642, U.S. Pat. No. 7,113,276, and US 2007/0000434, all of which are owned by the assignee of the present application and both of which are incorporated herein by reference in their entirety. The photoluminescence analysis is used for detection of low recombination lifetime areas in the sample 16 as low lifetime is observed whenever defects are present. Thus, the detection of low recombination lifetime areas in the sample 16 identifies defects in the sample 16. Particular applications are related to photoluminescence analysis of solar materials, for example, identification of contamination, low lifetime regions related to grain structure, electrical activity of grain boundaries, physical damage such as cracks, or electrical shunts are detected and quantified. Based on this quantification, the photoluminescence analysis technique can be used for solar cells binding to different quality classes. Specialized image processing and data transformation is used towards this goal. As an example, the processing may include statistical data segmentation (known also as clustering) or morphological image analysis to extract information on sample contamination, or analysis of grain boundaries or dependence of lifetime on grain structure, or detecting solar cell increased leakage areas or extracting metalized grid from the image and then performing the lifetime analysis or any combination of the above.

The defect data characteristic may be stored in memory 28 or displayed on a monitor 29 or other suitable display screen and/or may be printed out in hard copy form via a printer or similar device. If desired, the defect data characteristic may be converted into a visual image indicating the locations and quantity of defects in the sample 16. The visual image may be stored in memory 28 displayed on a monitor 29 or other suitable display screen and/or may be printed out in hard copy form via a printer or similar device.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method for using photoluminescence, comprising:
   directing excitation light at a sample, the sample emitting a photoluminescent light in response to the excitation light, a portion of the excitation light is reflected by or transmitted through the sample, wherein the photoluminescent light and the reflected or transmitted excitation light together form combined light;

filtering the combined light using a silicon filter to pass the photoluminescent light and to remove the excitation light;

detecting the photoluminescent light;

generating a defect data characteristic of the sample using the detected photoluminescent light; and storing the defect data characteristic of the sample.

2. The method of claim 1, wherein the photoluminescent light is in the infrared spectrum.

3. The method of claim 1, wherein the silicon filter is a silicon wafer.

4. The method of claim 1, wherein the silicon filter has introduced impurities that reduce recombination lifetime.

5. The method of claim 4, wherein the impurities are introduced to the silicon filter by ion implantation.

6. The method of claim 5, wherein the ion implantation is of at least one heavy metal.

7. The method of claim 6, wherein the intentional contamination with at least one heavy metal is performed by implantation with a dose in a range of 5E9 cm2 to 5e13 cm2.

8. The method of claim 4, wherein the impurities are introduced to the silicon filter by evaporation or sputtering of at least one heavy metal.

9. The method of claim 4, wherein the impurities are introduced to the silicon filter by doping with at least one of oxygen, carbon, and nitrogen during crystal growth followed by precipitation of the dopants through thermal annealing.

10. The method of claim 4, wherein the impurities are introduced to the silicon filter by doping without thermal annealing.

11. The method of claim 1, wherein the silicon filter includes an anti-reflective coating.

12. The method of claim 1, wherein the silicon filter is textured with a photonic crystal structure.

13. The method of claim 1, wherein the excitation light illuminates the full surface of the sample simultaneously.

14. The method of claim 1, wherein the sample is a solar cell material.

15. A photoluminescence imaging apparatus, comprising:
    a light source that generates excitation light for illuminating a sample;
    a silicon filter that filters light returned from the sample that includes photoluminescent light emitted by the sample in response to the excitation light and a portion of the excitation light reflected by or transmitted through the sample, the silicon filter removes the excitation light and passes the photoluminescent light; and
    a detector for detecting the photoluminescent light that passes through the silicon filter.

16. The apparatus of claim 15, wherein the photoluminescent light is in the infrared spectrum.

17. The apparatus of claim 15, wherein the silicon filter is a silicon wafer.

18. The apparatus of claim 15, wherein the silicon filter has a silicon filter having introduced impurities that reduce the recombination lifetime.

19. The apparatus of claim 18, wherein the impurities are introduced to the silicon filter by ion implantation.

20. The apparatus of claim 19, wherein the ion implantation is of at least one heavy metal.

21. The apparatus of claim 20, wherein the intentional contamination with at least one heavy metal is performed by implantation with a dose in a range of 5E9 cm2 to 5e13 cm2.

22. The apparatus of claim 18, wherein the impurities are introduced to the silicon filter by evaporation or sputtering of at least one heavy metal.

23. The apparatus of claim 18, wherein the impurities are introduced to the silicon filter by doping with at least one of oxygen, carbon, and nitrogen during crystal growth followed by precipitation of the dopants through thermal annealing.

24. The apparatus of claim 18, wherein the impurities are introduced to the silicon filter by doping without thermal annealing.

25. The apparatus of claim 15, wherein the silicon filter is textured with a photonic crystal structure.

26. The apparatus of claim 15, wherein the silicon filter has an anti-reflective coating.

27. The apparatus of claim 15, wherein the excitation light illuminates the full surface of the sample simultaneously.

28. The apparatus of claim 15, wherein the sample is a solar cell material.

29. A method of producing a photoluminescence system comprising:
    directing excitation light at a sample, the sample emitting a photoluminescent light with wavelengths centered around approximately 1100 nm in response to the excitation light, a portion of the excitation light is reflected by or transmitted through the sample, wherein the photoluminescent light and the reflected or transmitted excitation light together form combined light;
    filtering the combined light using a silicon filter, wherein filtering the combined light passes the photoluminescent light with wavelengths less than 1500 nm and removes the reflected or transmitted excitation light;
    detecting the photoluminescent light;
    generating a defect data characteristic of the sample using the detected photoluminescent light; and
    storing the defect data characteristic of the sample.

30. A photoluminescence imaging apparatus, comprising:
    a light source that generates excitation light for illuminating a sample;
    a silicon filter contaminated with at least one heavy metal to reduce the recombination lifetime, the silicon filter filters light returned from the sample, the light returned from the sample including photoluminescent light emitted by the sample in response to the excitation light and a portion of the excitation light reflected by or transmitted through the sample, the silicon filter removes the excitation light and passes the photoluminescent light; and
    a detector for detecting the photoluminescent light that passes through the silicon filter.

* * * * *